US00PP10231P

United States Patent [19]

DeWet

[11] Patent Number: Plant 10,231

[45] Date of Patent: Feb. 10, 1998

[54] PEAR ROOTSTOCK BP1

[75] Inventor: A. F. DeWet, deceased, late of Pretoria, South Africa, by Louisa Augusta Wilhelmina Catharina du Preez, executrix

[73] Assignee: Department of Agriculture, South Africa

[21] Appl. No.: 440,694

[22] Filed: May 15, 1995

[51] Int. Cl.[6] ..... A01H 5/00

[52] U.S. Cl. ..... Plt./36

[58] Field of Search ..... Plt./36

[56] References Cited

U.S. PATENT DOCUMENTS

P.P. 5,559 9/1985 Brooks ..... Plt./36
P.P. 6,362 11/1988 Brooks ..... Plt./36

OTHER PUBLICATIONS

Republic of South Africa, Certificate of grant of a Plant Breeder's Right, No. ZA 81099, Apr. 1, 1982.

*Primary Examiner*—James R. Feyrer
*Attorney, Agent, or Firm*—Chernoff, Vilhauer, McClung & Stenzel

[57] ABSTRACT

A new variety of pear rootstock selected from a family of seedling pear trees germinated from seed collected from a wild pear tree. The subject variety produces hearty semi-dwarf pear trees having high yield. The rootstock is compatible with all major commercial pear varieties. The variety roots easily and reproduces readily by hardwood cuttings.

2 Drawing Sheets

BACKGROUND AND SUMMARY OF THE INVENTION

The original plant of this new pear rootstock variety was a member of a family of approximately one hundred (100) seedling pear trees of unknown parentage which germinated from seeds collected in 1928 from a wild pear (*Pyrus communis*) at Elsenburg in the Republic of South Africa.

The subject seedling was selected in 1930 by Dr. A. F. DeWet, a former Research Horticulturist at the Fruit and Fruit Technology Research Institute at Stellenbosch, South Africa.

The BP1 rootstock has been tested and is now being released because of the high production of trees grafted thereon (Table 1) and the relative ease with which it roots. Trees on BP1 stocks in full bearing are approximately a quarter tree size less than those on seedling stocks and are considered semi-dwarf by comparison.

It has been virus-tested and is believed to be free of all known virus and virus-like diseases.

The new variety has been reproduced asexually by hardwood cuttings in Stellenbosch, South Africa. All subsequent generations have been true to form in all respects.

The following table compares trunk cross-sectional area and production of Packham's Triumph and Bon Chretien pear trees grown on the subject rootstock and four other rootstocks.

TABLE 1

The effect of five different rootstocks on truck cross-sectional area and production of Packham's Triumph and Bon Chretien.

| Rootstock | Trunk cross-sectional area ($cm^2$) | Cumulative production 12th leaf (kg/tree) | Production efficiency ($kg/cm^2$) |
|---|---|---|---|
| | Packham's Triumph | | |
| BP1 | 116,67 | 350,30 | 3,00 |
| BP2 | 140,31 | 368,10 | 3,62 |
| BP3 | 238,19 | 482,00 | 2,02 |
| Quince A | 64,82 | 141,20 | 2,18 |
| Seedling | 183,96 | 326,50 | 1,77 |
| | Bon Chretien | | |
| BP1 | 129,75 | 326,40 | 2,52 |
| BP2 | 228,03 | 382,40 | 1,68 |
| BP3 | 288,68 | 418,70 | 1,45 |
| Quince A | 774,46 | 146,10 | 1,96 |
| Seedling | 180,53 | 213,60 | 1,18 |

When compared to the O.H.X.F. variety #69, a patented clonal pear rootstock variety which produces trees similar in size to our BP1 variety, the following differences are noted:

| Character | BP1 | O.H.X.F. 69 |
|---|---|---|
| 1. Resistance to fire blight (*Erwinia amylovora*) | Average | Highly resistant |
| 2. Yield efficienty | Excellent (see table 1) | Average (similar) to seedling) |
| 3. Root anchorage | Good—but with a shallow root system | Excellent in all soils where grown |

-continued

| Character | BP1 | O.H.X.F. 69 |
|---|---|---|
| 4. Chilling requirement | Low | Average (normal for pears) |
| 5. Branching of current season growth | Few | Many |
| 6. Leaf shape | Ovate—rounded | Elliptic—pointed |
| 7. Buds | Waxy, smooth | Pubescent |
| 8. Fruit skin color | Yellow with pink over-color | Yellow with no over-color |
| 9. Fruit shape | Length and width are equal | Longer than wide |

DETAILED DESCRIPTION

The following is a detailed description of BP1 growth characteristics as observed on one-year-old shoots produced from hardwood cutting and on eight (8) year old stock plants growing at the research station site near Stellenbosch, South Africa. The characteristics described are those most often seen and used in the identification of a clonally propagated rootstock.

General color terms are used in accordance with their ordinary dictionary significance.

Description of Vegetative Characteristics

Terminology in accordance with S. B Jones & A. E. Luchsinger: Plant systematics, Sec. Ed 1987 McGraw-Hill International Editions.

Color: Color characteristics of the foliage, fruit, blossom, bark and fall leaf color of the sbject variety do not differ noticeably and are not unique when compared with other fruiting and rootstock varieties of *Pyrus communis*, except as noted.

Figure 1:
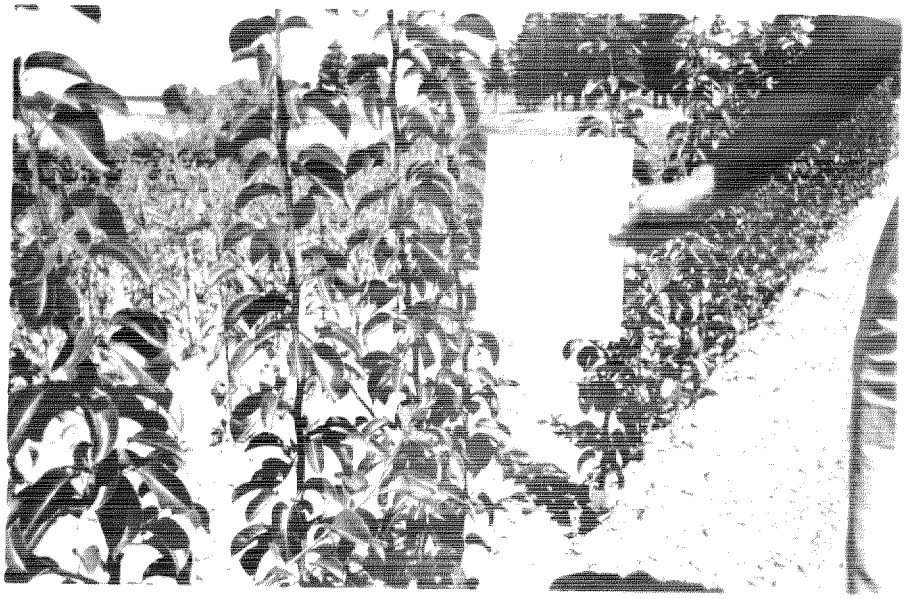
FIG. 1 shows a young tree of the subject variety.

General habit (FIG. 1):
- *Strength of growth.*—Vigorous, stiff.
- *Habit.*—Upright.
- *Branching.*—Few.

Vegetative shoots:
- *Bark color.*—Gray-brown.
- *Pubescence.*—Inconspicuous.
- *Lenticels.*—Medium.

Figure 2:
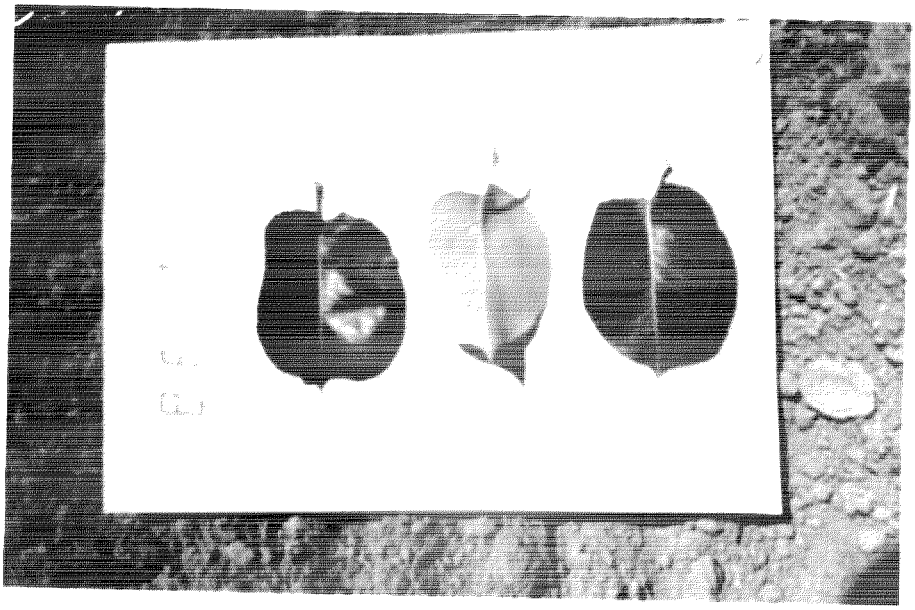
FIG. 2 shows leaves from a tree of the subject variety.

Leaves (FIG. 2):
- *Size.*—Average 96.2 mm × 52.5 mm.
- *Shape.*—Ovate.
- *Base.*—Rounded.
- *Apex.*—Accuminate.
- *Serrations.*—Serrate, Shallow.
- *Internode length.*—Average — 25 mm.
- *Arrangement.*—Alternate.
- *Color.*—Top surface — green; bottom surface — pale green.

Leaf scars:
- *Shape.*—Very Broad V.
- *Color.*—Dark Brown.

Petioles:
- *Shape.*—Slender, slightly channeled.
- *Length.*—Medium, 1–2 cm.
- *Color.*—Light Green.
- *Pose.*—Medium, 30–60 degrees.

Stipules:
- *Size.*—Medium 5–10 mm.
- *Color.*—Light Green.
- *Pose.*—Mostly reposed along petiole to slightly held out.
- *Margin.*—Entire.

Lateral buds:
- *Size.*—Medium.
- *Shape.*—Intermediate.
- *Color.*—Dark Brown.
- *Pubescence.*—Pubescent.

Apical buds:
- *Size.*—Larger than lateral buds.
- *Shape.*—Aristate.
- *Color.*—Dark Brown.
- *Pubescence.*—Tomentose.

Dormant Plant

Shoots:
- *Size.*—Diameter at base 1–1.5 cm, stiff.
- *Bark color.*—Orange brown to dark brown.
- *Pubescence.*—Inconspicuous.

Nodes: Very little larger in diameter than internodes with a shoulder underneath the leaf scar.
- *Internodes.*—Regularly spaced.
- *Distance between nodes.*—Average — 25 mm. Rooting characteristics: Relatively easy to root when compared to other clonally propagated pear (Pyrus) rootstocks.

Flower and Fruit Characteristics

Flowers:
- *Inflorescence.*—Mean number of flowers, 7.9 per lateral bud.
- *Flower type.*—Single.
- *Flower color.*—White.
- *Petal length.*—Mean 16.5 mm.
- *Shape of base of petal.*—Flat.
- *Sepal length.*—Medium.
- *Sepal position.*—Horizontal.
- *Stigma position as compared with the anthers.*—Above.
- *Anther size.*—Medium.
- *Anther count.*—Average — 16.
- *Anther color.*—Pale yellow.
- *Pollen.*—Functional.
- *Pedicel pubescence.*—Medium.

Fruit:
- *External evaluation when ripe.*—No commercial value.
- *Time of fruit ripening.*—Late January in Stellenbosch, South Africa.
- *Symmetry (in longitudinal section).*—Symmetric.
- *Shape (in profile view).*—Convex.
- *Position of maximum diameter.*—Towards middle.
- *Ground color of skin.*—Green-yellow.
- *Over-color of skin.*—Pink.
- *Amount of over-color.*—Slight.
- *Tendency to color by the sun.*—Little.
- *Amount of russet.*—Absent or very slight.
- *Number of lenticels.*—Medium.
- *Conspicuousness of lenticels.*—Conspicuous.

*Length of stalk.*—Medium.
*Thickness of stalk.*—Medium.
*Shape of stalk.*—Straight.
*Insertion of stalk.*—Along the axis.
*Cavity of stalk.*—Medium.
*Size of eye.*—Medium.
*Opening of eye.*—Intermediate.
*Pose of sepals.*—Convergent.
*Length of sepals.*—Medium.
*Depth of eye basin.*—Medium to deep.
*Width of eye basin.*—Medium.
*Margin of eye basin.*—Even.
*Length.*—55.5 mm.
*Diameter.*—54.9 mm.
*Size (length × diameter).*—3047.
*Mass (weight).*—110.7 g/fruit.

Fruit: Internal evaluation when ripe.
*Diameter of core.*—21.8 mm.
*Type of core.*—Normal.
*Shape of cells of core.*—Ovate.
*Shape of seeds.*—Ovate.
*Color of seed (dried).*—Dark brown.
*Texture of flesh.*—Medium.
*Juiciness of flesh.*—Weak to medium.
*Taste of flesh.*—Intermediate.
*Percent of sugar.*—14.6%.

General Characteristics

Figure 3:
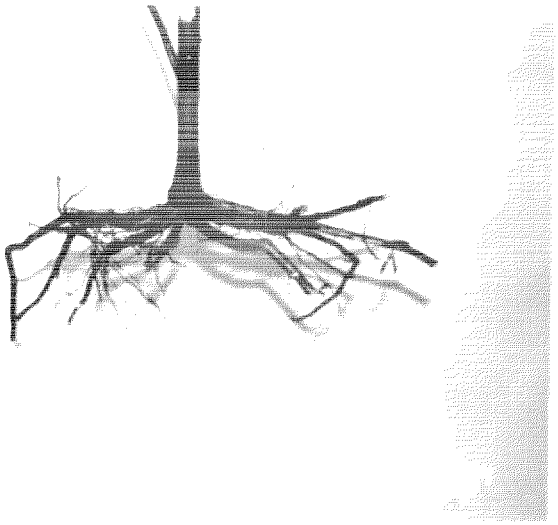
FIG. 3 shows the roots of a tree of the subject variety.

Root suckering: Very slight.
Dwarfing: Semi-dwarfing.
Precocity: Trees graftred on clone rootstocks bear earlier than on seeding rootstock.
Adaptability to soil type: Does well on sandy loam to clay loam soils.
Compatibility: Compatible with all major commerical pear cultivars.
Size control potential: Trees budded on BP1 will reach a size of approximately ¾ of the size or less at the stage of full production, compared to a tree of the same cultivar budded on BP3 and seedling rootstock
Root anchorage (FIG. 3): Good, but with a more shallow root system than a tree grown on seedling rootstock.
Hardiness: Hardy in most pear growing areas in South Africa. Tested and found free of all known virus diseases to pear.

General Guideline for Propagation

Most pear trees worldwide are established on *Pyrus communis* seedling rootstocks or seedling rootstocks of several other pear species.

The main disadvantage of seedling rootstocks is the variation in tree size, which makes it difficult to select a suitable planting system.

Trees on clonal rootstocks are generally more uniform is size, come into bearing sooner and are usually more precocious than trees on seedling rootstocks.

Research has shown that trees on clonally propagated BP1 rootstock perform far better than trees on seedling rootstocks in regard to precocity and production efficiency.

The BP1 pear rootstock is propagated most easily and successfully by use of hardwood cuttings. The advantages of BP1 propagation by cutting is that it is relatively simple and cheap in comparison to the stoolbed or tissue culture methods and is therefore recommended.

Better rooting is obtained from stock plant shoots that are produced near the root system. Stock plants should therefore be cut down to 20 cm or lower. Research has also shown that cuttings taken from BP1 stock plants on a dwarfing rootstck, like Quince A, root better. Burrknot development on the Quince A rootstock may cause premature death or decline in such stock plants and regular stock plant replacement may become necessary.

Stock plants on their own roots can also be planted for use in the mother block.

To Produce as many shoots as possible during the first or second growing season, shoots can be bent horizontally at a height of approximately fifty (50) cm. The upright shoots which develop can be used as cutting material. After the third year, this technique should no longer be necessary.

To ensure good light interception and correct shoot thickness, the stock plants can be cut back severely leaving stubs with two to three (2–3) buds and shoots can then be thinned for ideal shoot thickness. The ideal is to produce strong vigorous shoots longer than seventy (70) cm and with an average thickness of ten to fifteen (10–15) mm by the end of the growig season.

BP1 cuttings do not root as readily during the juvenile stage of stock plant development first two (2 ) years after stock plants which are three (3 ) years or older. Cuttings taken from stock plants which are too old and in a state of decline also root poorly.

BP1 stock plants have a low chilling requirement and can be established in a warm area where they will bud early and have a long growing period in which to accumulate good rooting reserves. Cuttings taken from stock plants growing in colder areas normally tend to bud-out before rooting has taken place. This can decrease the rooting "take" of BP1 stocks.

Contrary to the experience with most other plants, terminal BP1 cuttings root better than based cuttings. Research has shown that the optional length for BP1 hardwood cuttings is twenty-five to thirty (25–30) cm and the optional thickness for good rooting is ten to fifteen (10–15) mm.

The cuttings should be cutoff apically and basally near a bud (two (2) mm). This prevents cut die-back at the apical end and promotes better coating at the basal end.

Preparation and Handling of Cutting

The optimum time to cut BP1 cuttings for rooting is mid-April to mid-May in Stellenbosch, South Africa where research was conducted. Rooting is much reduced if cuttings are taken later.

Basal wounding (FIG. 1) in hardwood cuttings promote rooting. It is important to cut through the bark and wood and then to apply hormone treatment immediately after wounding so as to ensure effective uptake.

Sudo butyric acid (IBA) is applied at a four thousand (4000) mg/litter concentration by quick dip method (five (5) seconds). The alcohol/water solution is preferred because the powder preparation is not taken up as effectively. Cuttings should not be immersed deeper than the basal would (five to ten (5–10) mm). After the IBA treatment, the cuttings are left for ten to fifteen (10–15) minutes to dry before they are planted.

Sanitation must be maintained throughout the propagation chain. The cuttings and tools used can be treated with disinfectants or fungicides. Apical tips of cuttings should be sealed with a wound protection to prevent drying out and die-back.

Rooting

The direct plant (DP) method is used more successfully to root BP1 hardwood cuttings. No cold treatment is given with the DP method since it has been shown that cold storage at four (4) degrees centigrade for one (1) or more weeks can decrease rooting by up to fifteen (15) percent.

Soil preparation and management is very important to optimize the soil as a rooting medium.

BP1 cuttings are very sensitive to wet conditions during the rooting phase ad good drainage of excess water must be provided.

To limit moisture stress and improve rooting a good contact between the cutting and the soil medium must be ensured. Care should be taken not to compact the soil too much in the cutting rows and/or beds.

BP1 cuttings root best in warm, well drained sandy-loam soil. Very sandy soils with a low water-holding capacity of heavy clay soils that become too wet are less suitable.

With the DP method two-thirds (⅔) of the cutting is planted under the soil surface to prevent drying out.

During the early summer, the new growth is very sensitive to heat and provisions should be made to cool and/or shade the cutting rows or beds. Protection from strong drying winds should also be considered.

I claim:

1. A new variety of pear tree, referred to by the cultivar designation BP1, substantitally as herein shown and described, characterized particularly by its ability to serve as a rootstock for grafting of pear tree cultivar to produce semi-dwarf pear trees which have a very high yield efficiency, are hardly and are compatible with all major commercial pear varieties, also characterized by its early bearing habit and its ability to root easily and reproduce readily by negative means particularly by hardwood cuttings.

* * * * *

UNITED STATES PATENT AND TRADEMARK OFFICE

CERTIFICATE OF CORRECTION

PATENT NO. : Plant 10,231

DATED : February 10, 1998

INVENTOR(S) : Dr. A. F. DeWet

It is certified that error appears in the above-identified patent and that said Letters Patent is hereby corrected as shown below:

Col. 2, Line 3 Delete "truck" after "rootstocks on" insert --trunk--

Col. 3, Line 2 Under "Color" delete "sbject" after "fall leaf color of the" insert --subject--

Col. 6, Line 4 Delete "rootstck" insert --rootstock--

Col. 6 4th paragraph, last line, delete "growig" before "season" insert --growing--

Col. 6 8th paragraph, line 1, delete "cutoff" after "The cuttings should be..." insert --cut off--

Col. 6 11th paragraph, line 5, delete "would" after "basal" insert --wound--

Col. 7 3rd full paragraph, line 2, delete "ad" before "good drainage" insert --and--

Col. 7 5th full paragraph, line 2, delete "or" before "heavy clay" insert --of--

Col. 8 3rd paragraph, line 6, delete "hardly" before "and are compatible" insert -- hardy--

Signed and Sealed this

Twenty-seventh Day of October, 1998

*Attest:*

Bruce Lehman

BRUCE LEHMAN

*Attesting Officer*

*Commissioner of Patents and Trademarks*